United States Patent
Lou et al.

(10) Patent No.: US 9,681,845 B2
(45) Date of Patent: Jun. 20, 2017

(54) METHOD AND APPARATUS FOR SCANNING WITH LOWERED DOSE

(71) Applicant: Shenyang Neusoft Medical Systems Co., Ltd., Shenyang (CN)

(72) Inventors: Shanshan Lou, Shenyang (CN); Lixia Tong, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 255 days.

(21) Appl. No.: 14/578,485

(22) Filed: Dec. 22, 2014

(65) Prior Publication Data

US 2015/0173691 A1 Jun. 25, 2015

(30) Foreign Application Priority Data

Dec. 23, 2013 (CN) .......................... 2013 1 0719712

(51) Int. Cl.
*A61B 6/00* (2006.01)
*A61B 6/06* (2006.01)
*A61B 6/03* (2006.01)

(52) U.S. Cl.
CPC ............... *A61B 6/06* (2013.01); *A61B 6/032* (2013.01); *A61B 6/484* (2013.01); *A61B 6/542* (2013.01); *A61B 6/4078* (2013.01)

(58) Field of Classification Search
CPC ......... A61B 6/032; A61B 6/06; A61B 6/4078; A61B 6/484; A61B 6/542; A61B 5/7289;

(Continued)

(56) References Cited

U.S. PATENT DOCUMENTS 6,504,898 B1 * 1/2003 Kotler ...................... G21K 5/10
378/64
6,510,337 B1 * 1/2003 Heuscher ............... A61B 6/032
378/8

(Continued)

FOREIGN PATENT DOCUMENTS

| CN | 1846620 A | 10/2006 |
|---|---|---|
| CN | 101472381 A | 7/2009 |
| JP | 2000005160 A | 1/2000 |
| WO | 0079483 A1 | 12/2000 |

OTHER PUBLICATIONS

The first Office Action issued on Jul. 1, 2015 regarding the Chinese priority patent application (201310719712.4).

*Primary Examiner* — Irakli Kiknadze
(74) *Attorney, Agent, or Firm* — Kilpatrick Townsend & Stockton LLP

(57) ABSTRACT

A method and an apparatus for scanning with a lowered dose are provided. The method includes: determining a dynamic changing model of a prepatient collimator according to a rotation angle of a tube in a scanning mode; in a case that the scanning mode is a normal scan, controlling an opening angle of the prepatient collimator according to the dynamic changing model of the prepatient collimator at an initial stage and an end stage of the normal scan; and in a case that the scanning mode is a scan with phase control, controlling an opening angle of the prepatient collimator according to the dynamic changing model of the prepatient collimator at an initial stage and an end stage of a phase of the scan with phase control.

16 Claims, 6 Drawing Sheets

(58) Field of Classification Search
CPC ......... A61B 6/027; A61B 6/503; A61B 6/541; A61B 6/507; A61B 6/481; A61B 6/54; A61B 6/488; A61B 6/5205; A61B 6/4035; A61B 6/469; A61B 6/405; A61B 6/482; A61B 6/544; A61B 6/547; G05B 13/048; G05B 17/02; G05B 11/32; G05B 13/042; G05B 13/026; G05B 2219/40264; G05B 13/027; G05B 15/02; G05B 19/0428; G05B 2219/2639; G05B 23/0272; G05B 13/02; G05B 13/022; G05B 13/0245; G05B 13/0295; G05B 13/04
USPC ................................. 378/4, 19, 16, 147–153
See application file for complete search history.

(56) References Cited

U.S. PATENT DOCUMENTS

| | | | |
|---|---|---|---|
| 7,110,497 B2 * | 9/2006 | Halsmer | A61B 6/00 378/62 |
| 7,260,171 B1 * | 8/2007 | Arenson | A61B 6/032 378/16 |
| 7,583,775 B2 * | 9/2009 | Ozaki | G21K 1/04 250/370.11 |
| 2006/0177002 A1 | 8/2006 | Toth et al. | |
| 2009/0168951 A1 | 7/2009 | Yan | |
| 2012/0177175 A1 | 7/2012 | Bjorkholm | |

* cited by examiner

METHOD AND APPARATUS FOR SCANNING WITH LOWERED DOSE

This application claims priority to Chinese Patent Application No. 201310719712.4, entitled "METHOD AND APPARATUS FOR SCANNING WITH LOWERED DOSE", filed with the Chinese State Intellectual Property Office on Dec. 23, 2013, which is incorporated by reference in its entirety herein.

FIELD

The application relates to a method and an apparatus for scanning with a lowered dose.

BACKGROUND

An electronic computer X-ray tomography technique (CT) relates to a detection device for diseases with complete functions. The working principle of a CT scanner is as follows. The checked human body is measured by a high-sensitivity device based on different X-ray absorptance and transmittance of different tissues of the human body. The data obtained by the measurement is input into a computer, and a sectional image or a three-dimensional image of a checked body part of the human body is reconstructed after the data is processed by the computer. In this way, small lesions of the human body can be detected.

With the increasing usage of the CT scanner, people pay more and more attention to radiation damage of CT scanning Since the radiation damage is directly proportional to dose and the damage is increased as the dose is increased, various methods for reducing the does are proposed, for example, a method of changing scanning mode by remaining a voltage, lowering a current, increasing a pitch and adopting a self-adaptive dose modulation, or a method of obtaining a high does image from data obtained with a low dose scan by improving a reconstruction algorithm.

In order to reduce the does and radiation damage and ensure the quality of the reconstructed image without increasing computer processing amount, a new method for reducing the does is provided in the application.

SUMMARY

Embodiments of the application provide a method and an apparatus for scanning with a lowered dose, with which the does and thus the radiation damage are reduced and the quality of the reconstructed image are ensured without increasing computer processing amount.

Technical solutions of the application are as follows.

A method for scanning with a lowered dose includes:
determining a dynamic changing model of a prepatient collimator according to a rotation angle of a tube in a scanning mode;
in a case that the scanning mode is a normal scan, controlling an opening angle of the prepatient collimator according to the dynamic changing model of the prepatient collimator at an initial stage and an end stage of the normal scan; and
in a case that the scanning mode is a scan with phase control, controlling an opening angle of the prepatient collimator according to the dynamic changing model of the prepatient collimator at an initial stage and an end stage of a phase of the scan with phase control,
where the dynamic changing model of the prepatient collimator is a dynamic changing model of the prepatient collimator in a direction of an X-axis.

An apparatus for scanning with a lowered dose includes:
a determining unit, configured to determine a dynamic changing model of a prepatient collimator according to a rotation angle of a tube in a scanning mode; and
a control unit, configured to, in a case that the scanning mode is a normal scan, control an opening angle of the prepatient collimator according to the dynamic changing model of the prepatient collimator at an initial stage and an end stage of the normal scan; and
the control unit is further configured to, in a case that the scanning mode is a scan with phase control, control an opening angle of the prepatient collimator according to the dynamic changing model of the prepatient collimator at an initial stage and an end stage of a phase of the scan with phase control,
where the dynamic changing model of the prepatient collimator is a dynamic changing model of the prepatient collimator in a direction of an X-axis.

In the technical solutions of the application, usage of fanbeam channels (i.e., a dynamic changing model of a prepatient collimator) at different scanning stages are determined based on a rule in transition of a fanbeam to a parallel beam, and opening and closing of channels of the fanbeam are controlled based on the determined dynamic changing model of the prepatient collimator, to reduce the dose and to ensure the quality of the reconstructed image without increasing the computer processing amount of the image reconstruction.

BRIEF DESCRIPTION OF THE DRAWINGS

To better explain technical solutions in embodiments of the present application or in conventional technology, the drawings for the embodiments of the application and for the conventional technology are described briefly below. Apparently, the drawings described below are merely a few embodiments of the application. Other drawings may be obtained by those skilled in the art based on these drawings without any creative work.

DETAILED DESCRIPTION OF THE EMBODIMENTS

To better understand solutions of the application by those skilled in the art, embodiments of the application are described in detail below in conjunction with the drawings and implementations.

In scanning and reconstruction processes, sampling data obtained in a fanbeam scan is re-arranged to obtain simulated sampling data of a parallel beam, to reconstruct a scan image rapidly. The inventor found that there are some unused channels of the fanbeam (the unused channels may be interpreted as channels of the fanbeam not used in the conversion of the fanbeam to any angle of the parallel beam) at certain stages (mainly the initial stage and the end stage of the scan) in the conversion of the fanbeam to the parallel beam, and based on the above, opening and closing of fanbeam channels can be controlled, therefore, the dose can be reduced and the quality of the reconstructed image can be ensured.

The conversion relationship between a fanbeam and a parallel beam is described below in conjunction with FIGS. 1-4.

Figure 1:
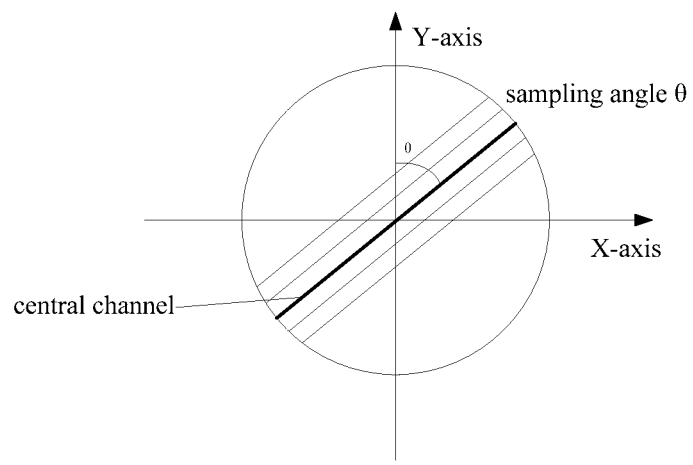
FIG. 1 is a schematic diagram of a parallel beam sampling according to the application.

FIG. 1 is a schematic diagram of a parallel beam sampling. The sampling angle θ of the parallel beam is an angle between a positive direction of a Y-axis and a central channel of the parallel beam. Sampling data of at least π angle is required to reconstruct an image, therefore, the sampling angle θ is at least in a range of [0,π].

Figure 2:
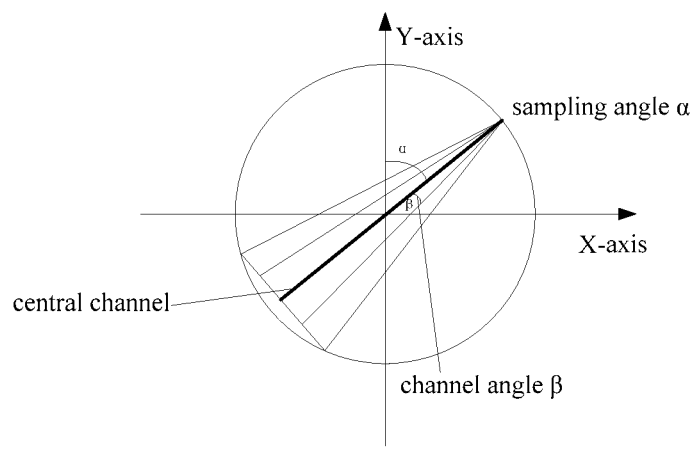
FIG. 2 is a schematic diagram of a fanbeam sampling according to the application.
Figure 3:
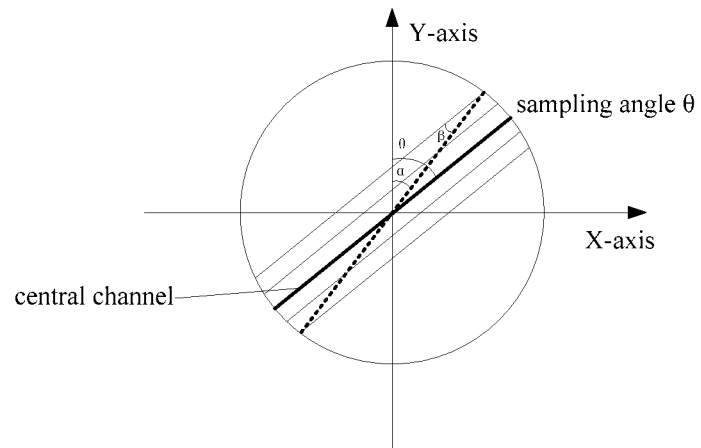
FIG. 3 is a schematic diagram of a conversion relationship between a fanbeam and a parallel beam according to the application.

FIG. 2 is a schematic diagram of a fanbeam sampling. The sampling angle α is an angle between a positive direction of a Y-axis and a central channel of a fanbeam. In conjunction with the conversion diagram of FIG. 3, the conversion relationship between the sampling angle θ of the parallel beam and the sampling angle α of the fanbeam is α=θ+β. Further, in conjunction with the range of the sampling angle θ of the parallel beam, the sampling angle α of the fanbeam is in a range of $[0,\pi+2\beta_{max}]$.

It is to be noted that $2\beta_{max}$ is the channel angle of the fanbeam. To ensure the fanbeams can be converted into equidistant parallel beams, a channel angle β between neighboring channels of the fanbeam is the same and the $2\beta_{max}$ channel angle of the fanbeam are distributed with the central channel as an axis. The channels are in a range of $[-\beta_{max}, \beta_{max}]$ (or in a range of $[0,2\beta_{max}]$, in this case, $-\beta_{max}$ is mapped to be 0, and $\beta_{max}$ is mapped to be $2\beta_{max}$. For convenience of illustration, $[-\beta_{max},\beta_{max}]$ is taken as an example below).

Figure 4:
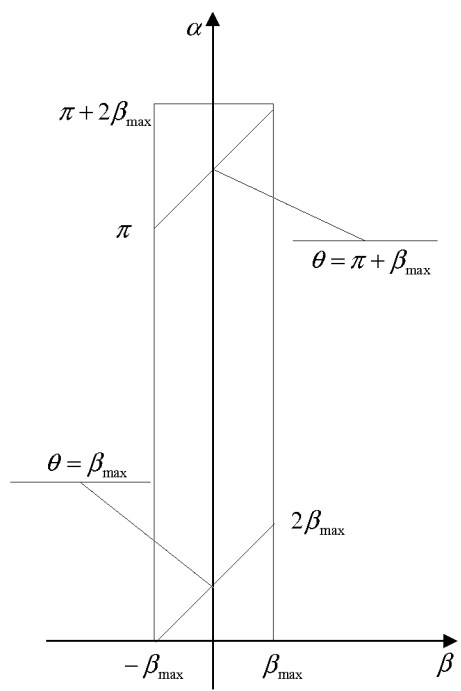
FIG. 4 is a schematic plan of a conversion relationship between a fanbeam and a parallel beam according to the application.

FIG. 4 is a schematic plan of a conversion relationship between the fanbeam and the parallel beam. The following three analyzing results can be obtained from FIG. 4.

(1) In a case that the sampling angle α is in a range of $[2\beta_{max},\pi]$, each channel in the range of $[-\beta_{max},\beta_{max}]$ can be converted into a sampling angle θ of a parallel beam, and the sampling data of the channel can be reorganized into the sampling data of the corresponding sampling angle θ. That is, to ensure the quality of the reconstructed image, each channel of the fanbeam should be open in a case that the sampling angle α is in a range of $[2\beta_{max},\pi]$.

(2) In a case that the sampling angle α is in a range of $[0,2\beta_{max})$ (i.e., the initial stage of the scan), not all the channels are used for sampling, so the channels can be controlled to be opened according to scanning sequence (i.e., the channel is opened before it is used), instead of controlling all the channels to be opened at the beginning of the scan as in the conventional condition. In this way, the dose is reduced and thus the radiation damage is reduced.

(3) In a case that the sampling angle α is in a range of $(\pi,\pi+2\beta_{max}]$ (i.e., the end stage of the scan), not all the channels are used for sampling, so the channels can be controlled to be closed according to scanning sequence (i.e., only the channels which are needed are open at the end stage of the scan), instead of controlling all the channels to be open until the scan is finished as in the conventional condition. In this way, the dose is reduced and thus the radiation damage is reduced.

A dynamic changing model of a prepatient collimator (also referred to as Aplane) can be obtained based on the analysis above. Therefore, a dynamic changing model of a prepatient collimator may be determined in the scan by combining with a rotation angle of a tube (i.e., an X-ray tube), and then an opening angle of the prepatient collimator, i.e. opening and closing of the fanbeam channels, may be controlled according to the dynamic changing model. The dynamic changing model of the prepatient collimator herein mainly refers to a dynamic changing model of a prepatient collimator in a direction of an X-axis.

Three implementations for scanning with a lowered dose are provided, which are described in detail below.

The First Implementation

Figure 5:
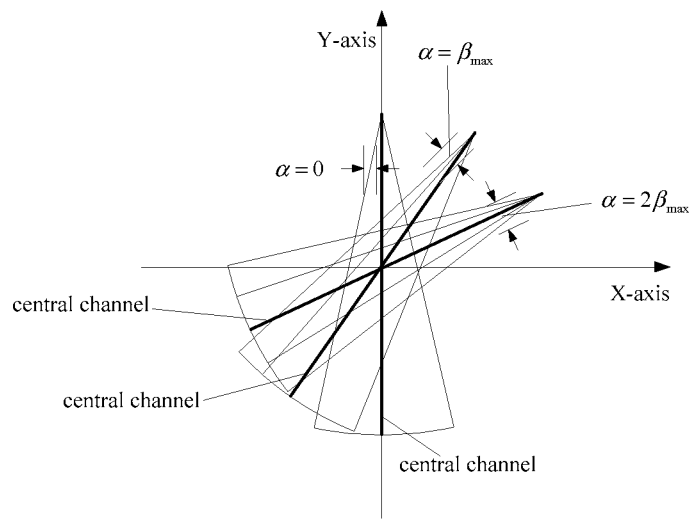
FIG. 5 is a schematic diagram of controlling channels to be opened according to the application.

In the implementation, the foregoing analyzing result (2) may be used to reduce the dose. That is, channels of the fanbeam are controlled to be opened one by one at the initial stage of the scan, and all the channels of the fanbeam are opened when the sampling angle α is equal to $2\beta_{max}$, to ensure the quality of the reconstructed image. In view of the above, a reasonable opening velocity (referred to as a first velocity herein) is set, to control the channels of the fanbeam to be opened in sequence in a direction from $-\beta_{max}$ to $\beta_{max}$ at the first velocity $V_1$ at the initial stage of the scan, as shown in FIG. 5.

Three embodiments are provided below for this implementation.

The First Embodiment

All the channels of the fanbeam are close at the beginning of the scan. A parameter $\alpha_{end}$ may be set to indicate a sampling angle when all the channels of the fanbeam become open. In the embodiment, $\alpha_{end}=2\beta_{max}$ (i.e., a theoretical value of the foregoing analysis). The fanbeam includes channels in a range of $2\beta_{max}$, that is, channels in the range of $2\beta_{max}$ need to be opened during the process that the sampling angle α is changed from 0 to $\alpha_{end}$, therefore, the first velocity is:

$$V_1 = \frac{2\beta_{max}}{\alpha_{end}} * \alpha - \beta_{max} = \alpha - \beta_{max}.$$

The Second Embodiment

In a case of a tomography scan, the data obtained at the beginning of the scan and the data obtained at the end of the scan may be inconsistent if the range of the sampling angle θ is π, due to moving or panting of the scanned object in the scan. In this case, the occurred redundant data is needed to be obtained in the sampling process. Therefore, the second embodiment and the third embodiment are provided to treat the redundant data.

$\alpha_{end}=2\beta_{max}$ in the first embodiment may be considered as a theoretical condition. In practice, to address the problem of redundant data, all the channels of the fanbeam may be controlled to be opened at a high velocity to shorten the time of opening the channels, i.e., all the channels of the fanbeam are opened before the sampling angle $\alpha$ reaches $2\beta_{max}$, in this case, $0<\alpha_{end}<2\beta_{max}$, and the first velocity $$V_1 = \frac{2\beta_{max}}{\alpha_{end}} * \alpha - \beta_{max}.$$

To ensure the reasonableness and smooth of the reconstructed image, a weighting process is performed on the redundant data. There are multiple designs for a weight $\omega(\alpha,\beta)$, which is not limited in the application, as long as the sum of weights of the sampling data of the same path is 1, i.e., $\omega(\alpha,\beta)+\omega(\alpha+\pi+2\beta,-\beta)=1$. For example, the weights of the sampling data obtained at 0° and 180° are set as 0.5 and 0.5 respectively, or the weights of the sampling data obtained at 1° and 181° are set as 0.3 and 0.7 respectively. The design of the weight may be selected as needed, which is not limited in the application.

The Third Embodiment

Besides the solution of the second embodiment, the third embodiment is also provided to obtain the occurred redundant data for processing. In the third embodiment, the opening velocity of the channels is not changed, but the number of the channels to be opened is decreased in stead. That is, at the initial stage of the scan, some of the channels in the range of $2\beta_{max}$ which are used firstly are controlled to be opened and some of the channels in the range of $2\beta_{max}$ which are used later are kept close. For example, channels $[-\beta_{max},\beta_{end}]$ are open and channels $(\beta_{end},\beta_{max}]$ are close. Because the opening velocity is not changed and the number of the channels to be opened is decreased, the time of opening the channels is shortened, and in this case, $\alpha_{end}=\beta_{max}-\beta_{end}$.

The first velocity of this embodiment is the same as the first velocity $V_1=\alpha-\beta_{max}$ of the first embodiment. The difference is that channels $[-\beta_{max},\beta_{max}]$ need to be opened from $-\beta_{max}$ in the first embodiment, and channels $[-\beta_{max},\beta_{max}]$ need to be opened from $\beta_{end}$ in this embodiment.

It is to be noted that the value of $\beta_{end}$ may be determined as needed. The time for opening the channels $[\beta_{end},\beta_{max}]$ is short as $\beta_{end}$ is close to $\beta_{max}$, and the time for opening the channels $[\beta_{end},\beta_{max}]$ is long as $\beta_{end}$ is close to $-\beta_{max}$. In a case of $\beta_{end}=-\beta_{max}$, which is the solution of the first embodiment, the dose is the least.

Similarly, to ensure the reasonableness and smooth of the reconstructed image, a weighting process is performed on the redundant data. There are multiple designs for a weight $\omega(\alpha,\beta)$, which is not limited in the application, as long as the sum of sampling data of the same path is 1, i.e., $\omega(\alpha,\beta)+\omega(\alpha+\pi+2\beta,-\beta)=1$.

The Second Implementation

Figure 6:
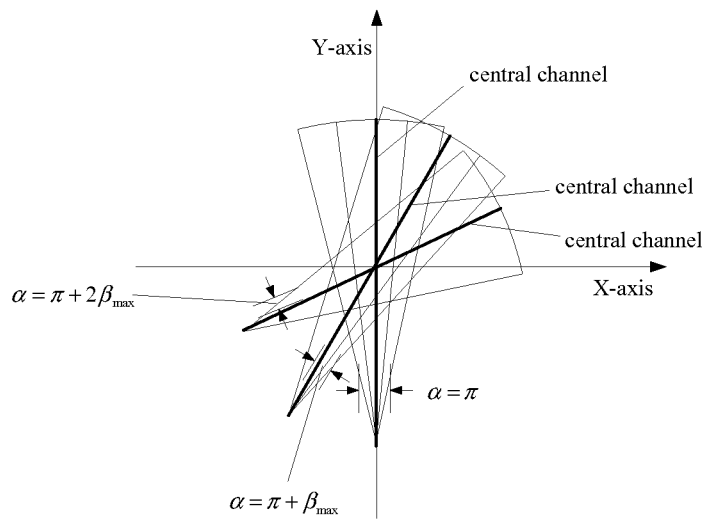
FIG. 6 is a schematic diagram of controlling channels to be closed according to the application.

In the implementation, the foregoing analyzing result (3) may be used to reduce the dose. That is, the channels of the fanbeam are controlled to be closed one by one at the end stage of the scan, and all the preset channels of the fanbeam (the preset channels are $[-\beta_{max},\beta_{max}]$, i.e., all the channels of the fanbeam, in the first embodiment and the second embodiment of the implementation; and the preset channels are $[-\beta_{max},\beta_{end}]$, i.e., the channels not used at the end stage of the sampling, in the third embodiment of the implementation, which will be described below) are closed when the sampling angle $\alpha$ is equal to $\alpha_{max}$. A reasonable closing velocity (referred to as a second velocity herein) is set to control the channels of the fanbeam to be closed in sequence in a direction from $-\beta_{max}$ to $\beta_{max}$ at the second velocity $V_2$ at the end stage of the scan, as shown in FIG. 6.

Similarly to the first implementation, three embodiments are provided below for this implementation.

The First Embodiment

This embodiment can also be considered as a theoretical condition, as the first embodiment of the first implementation. All the channels of the fanbeam are open before the end stage of the scan. A parameter $\alpha_{end}$ may be set to indicate the sampling angle when all the channels of the fanbeam become close. In the embodiment, $\alpha_{end}=2\beta_{max}$ (i.e., $(\pi+2\beta_{max})-\pi=2\beta_{max}$, which is also a theoretical value of the foregoing analysis). The channels to be closed in the whole process is all the channels in the range of $2\beta_{max}$, i.e., all the channels in the range of $2\beta_{max}$ need to be closed during the process that the sampling angle $\alpha$ is changed from $\pi$ to $\pi+2\beta_{max}$, therefore, the second velocity is:

$$V_2 = \frac{2\beta_{max}}{\alpha_{end}} * (\alpha - \alpha_{max}) + \beta_{max} = \alpha - \alpha_{max} + \beta_{max}.$$

The Second Embodiment

Similarly to the second embodiment of the first implementation, the dose can be reduced while addressing the problem of redundant data produced in the sampling in this embodiment.

In the embodiment, the problem of redundant data is addressed mainly by changing the closing velocity of the channels. That is, all the channels of the fanbeam are controlled to be closed at a high velocity to shorten the time of closing the channels. In this case, $\alpha_{end}<(\pi+2\beta_{max})-\pi=2\beta_{max}$, and the second velocity is:

$$V_2 = \frac{2\beta_{max}}{\alpha_{end}} * (\alpha - \alpha_{max}) + \beta_{max}.$$

Similarly to the second embodiment of first implementation, to ensure the reasonableness and smooth of the reconstructed image, $\omega(\alpha,\beta)+\omega(\alpha+\pi+2\beta,-\beta)=1$ needs to be ensured in the weighting process performed on the redundant data. The design for the weight may be selected as needed, which is not limited in the application.

The Third Embodiment

Besides the solution of the second embodiment, the third embodiment is also provided for addressing the problem of redundant data. In the third embodiment, the number of the channels to be closed is decreased to address the problem of redundant data. At the end stage of the scan, some of the channels in the range of $2\beta_{max}$ which are probably to be used are kept open and some of the channels in the range of $2\beta_{max}$ which are not used are closed. For example, opened channels $[-\beta_{max},\beta_{end}]$ are controlled to be closed one by one from $\alpha=\pi$, and channels $(\beta_{end},\beta_{max}]$ are kept open for scanning. Because the closing velocity is not changed and the number of the channels to be closed is decreased, the time of closing the channels is shortened, and in this case, $\alpha_{end}=\beta_{max}-\beta_{end}$.

The second velocity of this embodiment is the same as the second velocity $V_2=\alpha-\alpha_{max}+\beta_{max}$ of the first embodiment. The difference is that channels $[-\beta_{max},\beta_{max}]$ need to be closed from $-\beta_{max}$ in the first embodiment, and channels $[-\beta_{max},\beta_{end}]$ need to be closed from $-\beta_{max}$ in this embodiment.

It is to be noted that the value of $\beta_{end}$ may be determined as needed. The time for closing the channels $[-\beta_{max},\beta_{end}]$ is short as $\beta_{end}$ is close to $-\beta_{max}$, and the time for closing the channels $[-\beta_{max},\beta_{end}]$ is long as $\beta_{end}$ is close to $\beta_{max}$. In a case of $\beta_{end}=\beta_{max}$, which is the solution of the first embodiment, the dose is the least.

Similarly, to ensure the reasonableness and smooth of the reconstructed image, a weighting process is performed on the redundant data, and $\omega(\alpha,\beta)+\omega(\alpha+\pi+2\beta,-\beta)=1$ is ensured. The design of the weight may be selected as needed, which is not limited in the application.

The Third Implementation

In the first implementation, at the beginning of the scan, the channels of the fanbeam are close (all the channels are close as in the first and second embodiments, or only a few of channels are close as in third embodiment). At the initial stage of the scan (the sampling angle $\alpha$ is in a range of $[0,\alpha_{end}]$), the channels of the fanbeam are controlled to be opened in sequence in a direction from $\beta_{max}$ to $\beta_{max}$ (in a direction from $-\beta_{max}$ to $\beta_{max}$ as in the first and second embodiments, or in a direction from $\beta_{end}$ to $\beta_{max}$ as in the third embodiment. The starting points of the opening are different, but the directions of the opening are the same) at the first velocity $V_1$ and all the channels of the fanbeam are open in a case of $\alpha=\alpha_{end}$.

In the second implementation, at the end stage of the scan (the sampling angle $\alpha$ is in a range of $[\alpha_{max}-\alpha_{end},\alpha_{max}]$), the channels of the fanbeam are controlled to be closed in sequence in a direction from $-\beta_{max}$ to $\beta_{max}$ (in a direction from $-\beta_{max}$ to $\beta_{max}$ as in the first and second embodiments, or in a direction from $-\beta_{max}$ to $-\beta_{end}$ as in third embodiment. The ending points of the closing are different, but the directions of the closing are the same) at the second velocity $V_2$, and the channels of the fanbeam are close when $\alpha=\alpha_{max}$ (the channels of the fanbeam may be all the channels of the fanbeam as in the first and second embodiments, or may be a few of channels of the fanbeam as in third embodiment).

In the implementation, the dose is reduced by comprehensively utilizing the first and second implementations, i.e., utilizing both of the foregoing analyzing results (2) and (3). The controlling process may be as follows.

(1) Each channel of the fanbeam is controlled to be opened in sequence in a direction from $-\beta_{max}$ to $\beta_{max}$ at the first velocity in a case that a is in a range of $[0,\alpha_{end}]$, and all the channels of the fanbeam are open in a case of $\alpha=\alpha_{end}$.

(2) All the channels of the fanbeam are open in a case that a is in a range of $[\alpha_{end},\alpha_{max}-\alpha_{end}]$.

(3) Each channel of the fanbeam is controlled to be closed in sequence in a direction from $-\beta_{max}$ to $\beta_{max}$ at the second velocity in a case that a is in a range of $[\alpha_{max}-\alpha_{end},\alpha_{max}]$, and all the preset channels of the fanbeam are close in a case of $\alpha=\alpha_{max}$ (where $\alpha_{max}\geq\pi+2\beta_{max}$).

This implementation is described below by combing three embodiments.

The First Embodiment

The first embodiment illustrates a theoretical condition with an optimal effect of dose reducing, where $\alpha_{end}=2\beta_{max}$, and the process may be as follows.

(1) Each channel of the fanbeam is controlled to be opened in sequence in a direction from $-\beta_{max}$ to $\beta_{max}$ at the first velocity $V_1=\alpha-\beta_{max}$ in a case that a is in a range of $[0,2\beta_{max}]$, and all the channels of the fanbeam are open in a case of $\alpha=2\beta_{max}$.

(2) All the channels of the fanbeam are open in a case that a is in a range of $[2\beta_{max},\alpha_{max}-2\beta_{max}]$.

(3) Each channel of the fanbeam is controlled to be closed in sequence in a direction from $-\beta_{max}$ to $\beta_{max}$ at the second velocity $V_2=\alpha-\alpha_{max}+\beta_{max}$ in a case that $\alpha$ is in a range of $[\alpha_{max}-2\beta_{max},\alpha_{max}]$, and all the channels of the fanbeam are close in a case of $\alpha=\alpha_{max}$ (where $\alpha_{max}\geq\pi+2\beta_{max}$).

The Second Embodiment (1) Each channel of the fanbeam is controlled to be opened in sequence in a direction from $-\beta_{max}$ to $\beta_{max}$ at the first velocity $$V_1 = \frac{2\beta_{max}}{\alpha_{end}} * \alpha - \beta_{max}$$

in a case that a is in a range of $[0,\alpha_{end}]$ (where $0<\alpha_{end}<2\beta_{max}$), and all the channels of the fanbeam are open in a case of $\alpha=\alpha_{end}$.

(2) All the channels of the fanbeam are open in a case that $\alpha$ is in a range of $[\alpha_{end},\alpha_{max}-\alpha_{end}]$.

(3) Each channel of the fanbeam is controlled to be closed in sequence in a direction from $-\beta_{max}$ to $\beta_{max}$ at the second velocity $$V_2 = \frac{2\beta_{max}}{\alpha_{end}} * (\alpha - \alpha_{max}) + \beta_{max}$$

in a case that $\alpha$ is in a range of $[\alpha_{max}-\alpha_{end},\alpha_{max}]$, and all the channels of the fanbeam are close in a case of $\alpha=\alpha_{max}$.

Figure 7:
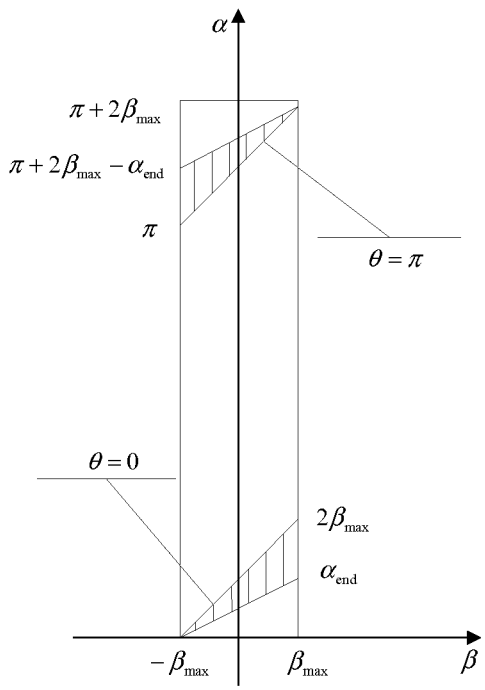
FIG. 7 is a schematic plan of a conversion relationship between a fanbeam with redundant data and a parallel beam according to the application.

As described above, to ensure the reasonableness and smooth of the reconstructed image in the tomography image reconstruction, a weighting process is performed on the redundant data (as the dashed area of the schematic diagram in FIG. 7). For example, one design of the weight $\omega(\alpha,\beta)$ may be as follows:

$$\omega(\alpha, \beta) = \begin{cases} \dfrac{\alpha}{2\beta_{max}+2\beta} - \dfrac{\alpha_{end}}{4\beta_{max}} & \dfrac{\alpha_{end}}{2\beta_{max}}(\beta+\beta_{max}) < \alpha < \dfrac{4\beta_{max}-\alpha_{end}}{2\beta_{max}}(\beta+\beta_{max}) \\ 1 & \dfrac{4\beta_{max}-\alpha_{end}}{2\beta_{max}}(\beta+\beta_{max}) \le \alpha < \dfrac{4\beta_{max}-\alpha_{end}}{2\beta_{max}}(\beta-\beta_{max})+\pi+2\beta_{max} \\ \dfrac{2\beta_{max}+\pi-\alpha}{2\beta_{max}-2\beta} + \dfrac{\alpha_{end}}{4\beta_{max}} & \dfrac{4\beta_{max}-\alpha_{end}}{2\beta_{max}}(\beta-\beta_{max})+\pi+2\beta_{max} \le \alpha < \dfrac{\alpha_{end}}{2\beta_{max}}(\beta-\beta_{max})+\pi+2\beta_{max} \\ 0 & \text{else} \end{cases}$$

There are two extremas $\alpha_{end}=0$ and $\alpha_{end}=2\beta_{max}$ in the design of the weight above.

In a case of $\alpha_{end}=0$, all the channels are open at the beginning of the scan, which is the conventional technology. In this case, the dose is not reduced, and the weight is:

$$\omega(\alpha, \beta) = \begin{cases} \dfrac{\alpha}{2\beta_{max}+2\beta} & 0 < \alpha < 2(\beta+\beta_{max}) \\ 1 & 2(\beta+\beta_{max}) \le \alpha < \pi+2\beta \\ \dfrac{2\beta_{max}+\pi-\alpha}{2\beta_{max}-2\beta} & \pi+2\beta \le \alpha < \pi+2\beta_{max} \\ 0 & \text{else} \end{cases}$$

In a case of $\alpha_{end}=2\beta_{max}$, all the channels are close at the beginning of the scan, which is the theoretical condition in the application. In this case, the dose is reduced most, i.e., the optimal effect of dose reducing, and the weight is:

$$\omega(\alpha, \beta) = \begin{cases} 1 & (\beta+\beta_{max}) \le \alpha < \pi+\beta+\beta_{max} \\ 0 & \text{else} \end{cases}$$

The Third Embodiment (1) The channels $[\beta_{end}, \beta_{max}]$ of the fanbeam are controlled to be opened in sequence in a direction from $\beta_{end}$ to $\beta_{max}$ at the first velocity $V_1 = \alpha - \beta_{max}$ in a case that the sampling angle $\alpha$ is in a range of $[0, \alpha_{end}]$ (where $\alpha_{end} = \beta_{max} - \beta_{end}$, the channels $[-\beta_{max}, \beta_{end}]$ are open and the channels $[\beta_{end}, \beta_{max}]$ are close), and all the channels of the fanbeam are open in a case of $\alpha = \alpha_{end}$.

(2) All the channels of the fanbeam are open in a case that $\alpha$ is in a range of $[\alpha_{end}, \alpha_{max} - \alpha_{end}]$.

(3) The preset channels between $[-\beta_{max}, \beta_{end}]$ of the fanbeam are controlled to be closed in sequence in a direction from $-\beta_{max}$ to $\beta_{end}$ at the second velocity $V_2 = \alpha + \alpha_{max} + \beta_{max}$ in a case that a is in a range of $[\alpha_{max} - \alpha_{end}, \alpha_{max}]$, and all the preset channels of the fanbeam are close in a case of $\alpha = \alpha_{max}$.

Figure 8:
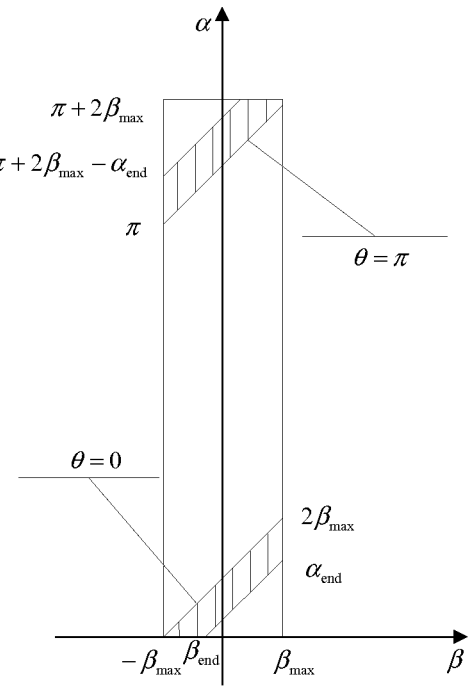
FIG. 8 is another schematic plan of a conversion relationship between a fanbeam with redundant data and a parallel beam according to the application.

As described above, to ensure the reasonableness and smooth of the reconstructed image in the tomography image reconstruction, a weighting process is performed on the redundant data (as the dashed area of the schematic diagram in FIG. 8). For example, one design of the weight $\omega(\alpha, \beta)$ may be as follows:

$$\omega(\alpha, \beta) = \begin{cases} \dfrac{\alpha - h}{\alpha_2 - h_1} & h_1 < \alpha < \alpha_2 \\ 1 & \alpha_2 \le \alpha < \alpha_3 \\ \dfrac{\alpha - h_2}{\alpha_3 - h_2} & \alpha_3 \le \alpha < h_2 \\ 0 & \text{else} \end{cases},$$

where $h_1 = \max(0, \alpha_1)$, $\alpha_1 = \beta - \beta_{max} + \alpha_{end}$, $h_2 = \min(\alpha_4, \pi + 2\beta_{max})$, $\alpha_4 = \beta + \beta_{max} + \pi + 2\beta_{max} - \alpha_{end}$, $\alpha_2 = \dfrac{4\beta_{max} - \alpha_{end}}{2\beta_{max}}(\beta + \beta_{max})$, and $\alpha_3 = \dfrac{4\beta_{max} - \alpha_{end}}{2\beta_{max}}(\beta + \beta_{max}) + \pi - 2\beta_{max} + \alpha_{end}$.

There are two extremas $\beta_{end} = \beta_{max}$ and $\beta_{end} = \beta_{max}$ in the design of the weight above.

In a case of $\beta_{end} = \beta_{max}$, all the channels are open at the beginning of the scan, which is the conventional technology. In this case, the dose is not reduced, and the weight is:

$$\omega(\alpha, \beta) = \begin{cases} \dfrac{\alpha}{2\beta_{max}+2\beta} & 0 < \alpha < 2(\beta+\beta_{max}) \\ 1 & 2(\beta+\beta_{max}) \le \alpha < \pi+2\beta \\ \dfrac{2\beta_{max}+\pi-\alpha}{2\beta_{max}-2\beta} + \dfrac{\alpha_{end}}{4\beta_{max}} & \pi+2\beta \le \alpha < \pi+2\beta_{max} \\ 0 & \text{else} \end{cases}.$$

In a case of $\beta_{end} = -\beta_{max}$, all the channels are close at the beginning of the scan, which is the theoretical condition in the application. In this case, the dose is reduced most, i.e., the optimal effect of dose reducing, and the weight is:

$$\omega(\alpha, \beta) = \begin{cases} 1 & (\beta+\beta_{max}) \le \alpha < \pi+\beta+\beta_{max} \\ 0 & \text{else} \end{cases}.$$

Figure 9:
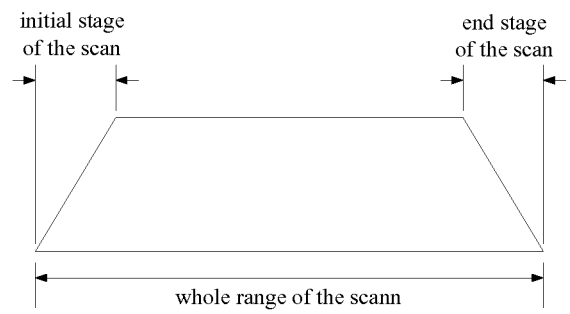
FIG. 9 is a schematic diagram of each stage of a normal scan according to the application.
Figure 10:
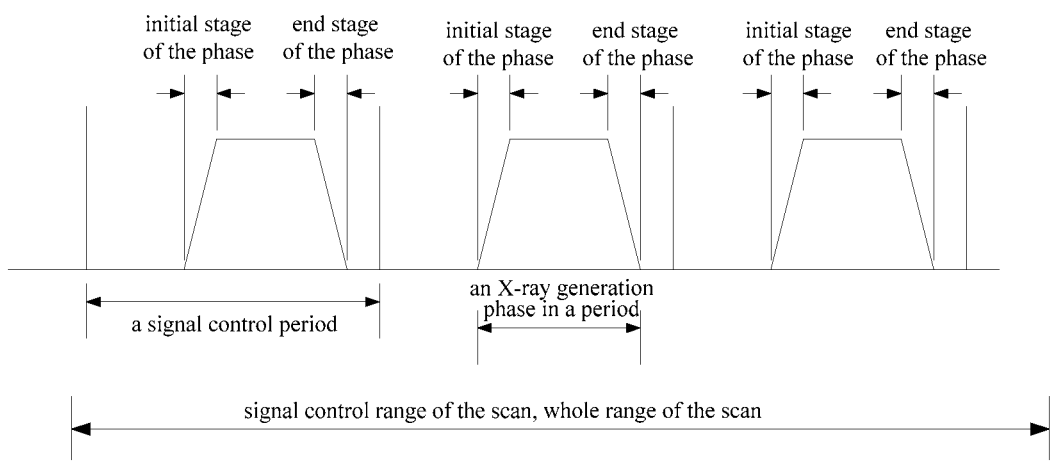
FIG. 10 is a schematic diagram of each stage of a scan with phase control according to the application.
Figure 11:
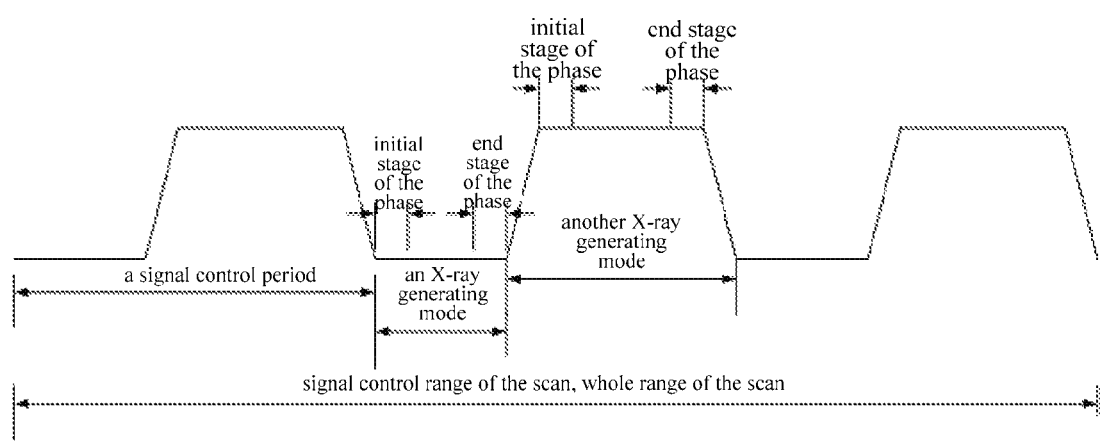
FIG. 11 is another schematic diagram of each stage of a scan with phase control according to the application.

It is to be noted that the solutions of the application are applicable to the normal scanning mode as illustrated in FIG. 9, and also applicable to a special scanning mode with phase control as illustrated in FIG. 10 and FIG. 11. The processes of these two scanning modes are described below in conjunction with FIGS. 9, 10 and 11.

The normal scanning mode illustrated in FIG. 9 is applicable to a routine scan of human body. The scanner maintains normal operating. At the data collection stage, the tube generates X-ray continuously (i.e., a high voltage or a high current is always applied to the tube). In this scanning mode, to reduce the dose, the channels may be controlled to be opened in sequence at the initial stage of the scan, and then maintain the state (i.e., all the channels are open) until the end stage during which the channels are closed in sequence, as the solutions in the application. The detailed process may refer to the description above, which is omitted herein.

FIGS. 10 and 11 illustrate two examples of a scan with phase control respectively. In the scan with phase control, at the data collection phase, the tube generates X-ray regularly according to a predefined phase range (i.e., the signal control period illustrated in FIGS. 10 and 11). It is to be noted that the predefined phase range may be periodic or aperiodic. The periodic phase range may include a fixed periodic phase range or a non-fixed periodic phase range. The phase range may be determined based on the object to be scanned and is not limited in the application.

The first example of the scan with phase control shown in FIG. 10 is mainly used for heart. There is a relatively stable range in the process of heart beating, and clear images can be obtained during that range. Therefore, an X-ray generation phase (the trapezoidal area in FIG. 10) may be determined according to the condition of heart beating, and a high voltage or a high current is applied to the tube in the X-ray generation phase, to ensure the tube to generate X-ray continuously.

In the case of FIG. 10, in a signal control period, the tube does not generate X-ray in some time (the horizontal line in each control period in FIG. 10, the data collected when the tube does not generate X-ray is invalid data), and the tube always generates X-ray in the X-ray generation phase. In the scan, the channels may be controlled to be opened in sequence at the initial stage, and then maintain the open state until the end stage at which the channels are closed in sequence, as the solutions in the application. The detailed process may refer to the description above and is omitted herein.

The second example of the scan with phase control shown in FIG. 11 is mainly used for special tissue. Different scanning images of the tissue may be obtained under different scanning voltage, and the patient's condition can be analyzed by comparing the differences between the different voltages. Therefore, at least two X-ray generation phases are set in a signal control period, and the X-ray is generated in a different way in each X-ray generation phase, for example, applying different voltages to the tube. It is to be noted that in each X-ray generation phase, the channels may be controlled to be opened in sequence at the initial stage, and then maintain the open state until the end stage at which the channels are closed in sequence, as the solutions in the application. The detailed process may refer to the description above and is omitted herein.

It is to be noted that the duration of the X-ray generation phase (i.e., the ratio of the X-ray generation phase to the signal control period) in FIGS. 10 and 11 may be determined according to practical conditions, which is not limited in the application.

Corresponding to the method described above, an apparatus for scanning with a lowered dose is further provided in the application. The apparatus includes:

a determining unit, configured to determine a dynamic changing model of a prepatient collimator according to a rotation angle of a tube in a scanning mode;

a control unit, configured to, in a case that the scanning mode is a normal scan, control an opening angle of the prepatient collimator according to the dynamic changing model of the prepatient collimator at an initial stage and an end stage of the normal scan; and the control unit is further configured to, in a case that the scanning mode is a scan with phase control, control an opening angle of the prepatient collimator according to the dynamic changing model of the prepatient collimator at an initial stage and an end stage of a phase of the scan with phase control.

The dynamic changing model of the prepatient collimator determined by the determining unit may be a dynamic changing model of the prepatient collimator in a direction of an X-axis.

In a fanbeam scanning, a sampling angle $\alpha$ is an angle between a positive direction of a Y-axis and a central channel of a fanbeam, where a is in a range of $[0, \alpha_{max}]$, $\alpha_{max} \geq \pi +$ $2\beta_{max}$; the fanbeam includes channels in a range of $[-\beta_{max}, \beta_{max}]$ with the central channel as an axis; the control unit includes:

a first control sub-unit, configured to control each of the channels of the fanbeam to be opened in sequence in a direction from $-\beta_{max}$ to $\beta_{max}$ at a first velocity in a case that a is in a range of $[0, \alpha_{end}]$, where all of the channels of the fanbeam are open in a case of $\alpha = \alpha_{end}$; and/or, a second control sub-unit, configured to control each of the channels of the fanbeam to be closed in sequence in a direction from $-\beta_{max}$ to $\beta_{max}$ at a second velocity in a case that $\alpha$ is in a range of $[\alpha_{max} - \alpha_{end}, \alpha_{max}]$, where all of preset channels of the fanbeam are close in a case of $\alpha = \alpha_{max}$.

Corresponding to the first and second embodiments of the first implementation of the method described above, the first control sub-unit is configured to control each of the channels of the fanbeam to be opened in sequence in a direction from $-\beta_{max}$ to $\beta_{max}$ at the first velocity $$V_1 = \frac{2\beta_{max}}{\alpha_{end}} * \alpha - \beta_{max}$$

in a case of $0 < \alpha_{end} \leq 2\beta_{max}$.

Corresponding to the first and second embodiments of the second implementation of the method described above, the second control sub-unit is configured to control each of the channels of the fanbeam to be closed in sequence in a direction from $-\beta_{max}$ to $\beta_{max}$ at the second velocity $$V_2 = \frac{2\beta_{max}}{\alpha_{end}} * (\alpha - \alpha_{max}) + \beta_{max}$$

in a case of $0 < \alpha_{end} < 2\beta_{max}$.

The solutions of the first and second embodiments of the third implementation of the method described above may be implemented by cooperation of the first control sub-unit and the second control sub-unit.

Corresponding to the third embodiment of the first implementation of the method described above, in a case that channels $[-\beta_{max}, \beta_{end}]$ are open, channels $(\beta_{end}, \beta_{max}]$ are close, and $\alpha_{end} = \beta_{max} - \beta_{end}$, the first control sub-unit is configured to control channels $[\beta_{end}, \beta_{max}]$ of the fanbeam to be opened in sequence in a direction from $\beta_{end}$ to $\beta_{max}$ at the first velocity $V_1 = \alpha - \beta_{max}$.

Corresponding to the third embodiment of the second implementation of the method described above, in a case that channels $[-\beta_{max}, \beta_{end}]$ are open, channels $(\beta_{end}, \beta_{max}]$ are close, and $\alpha_{end} = \beta_{max} - \beta_{end}$, the second control sub-unit is configured to control preset channels $[\beta_{max}, \beta_{end}]$ of the fanbeam to be closed in sequence in a direction from $-\beta_{max}$ to $\beta_{end}$ at the second velocity $V_2 = \alpha - \beta_{max} - \pi$.

The solution of the third embodiment of third implementation of the method described above may be implemented by cooperation of the first control sub-unit and the second control sub-unit.

The solutions in the application may be described in a general context of executable computer instructions executed by a computer, for example, a program unit. Generally, the program unit includes routines, programs, objects, components, data structures etc., for performing particular tasks or implementing particular abstract data types. The solutions in the application may also be carried out in a distributed computing environment. In the distributed computing environment, the tasks are performed by remote processing devices connected through a communication network. In the distributed computing environment, the program unit may be located in local or remote storage media including memory devices.

The embodiments in the specification are described in a progressive way. The same or similar parts of the embodiments may refer to each other. The description of each embodiment focuses on the difference from other embodiments. Especially, the description of the embodiments of the apparatus is brief due to the similarity to the embodiments of the method, and related information may be found in the description of the embodiments of the method. The embodiments of the apparatus described above are only schematic, the units described as separate components may be or be not physically separate, and the components presented as units may be or be not physical units located in a place or distributed on a plurality of network elements. A few or all the modules may be chosen based on practical needs to achieve the purpose of the solutions of the embodiments, which can be understood and performed by a person having ordinary skill in the art without paying any creative work.

The embodiments in the application are described above in detail. The application is described by specific implementations. The description of the embodiments is to help understanding the method and the apparatus in the application. For a person having ordinary skill in the art, there are modifications in specific implementations and applications according to the idea in the application. Therefore, the specification should not be understood as the limit of the invention.

The invention claimed is:

1. A method for scanning with a lowered dose, comprising:

determining a dynamic changing model of a prepatient collimator according to a rotation angle of a tube in a scanning mode;
in a case that the scanning mode is a normal scan, controlling an opening angle of the prepatient collimator according to the dynamic changing model of the prepatient collimator at an initial stage and an end stage of the normal scan; and
in a case that the scanning mode is a scan with phase control, controlling an opening angle of the prepatient collimator according to the dynamic changing model of the prepatient collimator at an initial stage and an end stage of a phase of the scan with phase control,
wherein the dynamic changing model of the prepatient collimator is a dynamic changing model of the prepatient collimator in a direction of an X-axis;
in a fanbeam scan, a sampling angle $\alpha$ is an angle between a positive direction of a Y-axis and a central channel of a fanbeam, wherein $\alpha$ is in a range of $[0, \alpha_{max}]$, $\alpha_{max} \geq \pi + 2\beta_{max}$; the fanbeam comprises channels in a range of $[-\beta_{max}, \beta_{max}]$ with the central channel as an axis; the dynamic changing model of the prepatient collimator is:
controlling each of the channels of the fanbeam to be opened in sequence in a direction from $-\beta_{max}$ to $\beta_{max}$ at a first velocity in a case that a is in a range of $[0, \alpha_{end}]$, wherein all of the channels of the fanbeam are open in a case of $\alpha = \alpha_{end}$; and/or
controlling each of the channels of the fanbeam to be closed in sequence in a direction from $-\beta_{max}$ to $\beta_{max}$ at a second velocity in a case that a is in a range of $[\alpha_{max} - \alpha_{end}, \alpha_{max}]$, wherein all of the channels of the fanbeam are close in a case of $\alpha = \alpha_{max}$.

2. The method according to claim 1, wherein
in a case of $0 < \alpha_{end} \leq 2\beta_{max}$, the first velocity $$V_1 = \frac{2\beta_{max}}{\alpha_{end}} * \alpha - \beta_{max}.$$

3. The method according to claim 2, wherein, in a case of $0 < \alpha_{end} \leq 2\beta_{max}$, $\alpha_{max} = \pi + 2\alpha_{max}$ and a tomography scan, the method further comprises:

setting a weight $\omega(\alpha, \beta)$ of sampling data corresponding to the sampling angle $\alpha$ and the channel $\beta$ as follows:

$$\omega(\alpha, \beta) = \begin{cases} \frac{\alpha}{2\beta_{max} + 2\beta} - \frac{\alpha_{end}}{4\beta_{max}} & \frac{\alpha_{end}}{2\beta_{max}}(\beta + \beta_{max}) < \alpha < \frac{4\beta_{max} - \alpha_{end}}{2\beta_{max}}(\beta + \beta_{max}) \\ 1 & \frac{4\beta_{max} - \alpha_{end}}{2\beta_{max}}(\beta + \beta_{max}) \leq \alpha < \frac{4\beta_{max} - \alpha_{end}}{2\beta_{max}}(\beta - \beta_{max}) + \pi + 2\beta_{max} \\ \frac{2\beta_{max} + \pi - \alpha}{2\beta_{max} - 2\beta} + \frac{\alpha_{end}}{4\beta_{max}} & \frac{4\beta_{max} - \alpha_{end}}{2\beta_{max}}(\beta - \beta_{max}) + \pi + 2\beta_{max} \leq \alpha < \frac{\alpha_{end}}{2\beta_{max}}(\beta - \beta_{max}) + \pi + 2\beta_{max} \\ 0 & \text{else} \end{cases}.$$

4. The method according to claim 1, wherein
in a case of $0 < \alpha_{end} \leq 2\beta_{max}$, the second velocity $$V_2 = \frac{2\beta_{max}}{\alpha_{end}} * (\alpha - \alpha_{max}) + \beta_{max}.$$

5. The method according to claim 4, wherein, in a case of $0 < \alpha_{end} \leq 2\beta_{max}$, $\alpha_{max} = \pi + 2\beta_{max}$ and a tomography scan, the method further comprises:
setting a weight $\omega(\alpha, \beta)$ of sampling data corresponding to the sampling angle $\alpha$ and the channel $\beta$ as follows:

$$\omega(\alpha,\beta) = \begin{cases} \dfrac{\alpha}{2\beta_{max}+2\beta} - \dfrac{\alpha_{end}}{4\beta_{max}} & \dfrac{\alpha_{end}}{2\beta_{max}}(\beta+\beta_{max}) < \alpha < \dfrac{4\beta_{max}-\alpha_{end}}{2\beta_{max}}(\beta+\beta_{max}) \\ 1 & \dfrac{4\beta_{max}-\alpha_{end}}{2\beta_{max}}(\beta+\beta_{max}) \le \alpha < \dfrac{4\beta_{max}-\alpha_{end}}{2\beta_{max}}(\beta-\beta_{max})+\pi+2\beta_{max} \\ \dfrac{2\beta_{max}+\pi-\alpha}{2\beta_{max}-2\beta} + \dfrac{\alpha_{end}}{4\beta_{max}} & \dfrac{4\beta_{max}-\alpha_{end}}{2\beta_{max}}(\beta-\beta_{max})+\pi+2\beta_{max} \le \alpha < \dfrac{\alpha_{end}}{2\beta_{max}}(\beta-\beta_{max})+\pi+2\beta_{max} \\ 0 & \text{else} \end{cases}.$$

6. The method according to claim 1, wherein, in a case of $0<\alpha_{end}\le 2\beta_{max}$, $\alpha_{max}=\pi+2\beta_{max}$ and a tomography scan, the method further comprises:

setting a weight $\omega(\alpha,\beta)$ of sampling data corresponding to the sampling angle $\alpha$ and the channel $\beta$ as follows:

$$\omega(\alpha,\beta) = \begin{cases} \dfrac{\alpha}{2\beta_{max}+2\beta} - \dfrac{\alpha_{end}}{4\beta_{max}} & \dfrac{\alpha_{end}}{2\beta_{max}}(\beta+\beta_{max}) < \alpha < \dfrac{4\beta_{max}-\alpha_{end}}{2\beta_{max}}(\beta+\beta_{max}) \\ 1 & \dfrac{4\beta_{max}-\alpha_{end}}{2\beta_{max}}(\beta+\beta_{max}) \le \alpha < \dfrac{4\beta_{max}-\alpha_{end}}{2\beta_{max}}(\beta-\beta_{max})+\pi+2\beta_{max} \\ \dfrac{2\beta_{max}+\pi-\alpha}{2\beta_{max}-2\beta} + \dfrac{\alpha_{end}}{4\beta_{max}} & \dfrac{4\beta_{max}-\alpha_{end}}{2\beta_{max}}(\beta-\beta_{max})+\pi+2\beta_{max} \le \alpha < \dfrac{\alpha_{end}}{2\beta_{max}}(\beta-\beta_{max})+\pi+2\beta_{max} \\ 0 & \text{else} \end{cases}.$$

7. The method according to claim 1, wherein, in a case that channels $[-\beta_{max}, \beta_{end}]$ are open, channels $(\beta_{end}, \beta_{max}]$ are close, and $\alpha_{end}=\beta_{max}-\beta_{end}$, controlling each of the channels of the fanbeam to be opened in sequence in a direction from $-\beta_{max}$ to $\beta_{max}$ at the first velocity comprises:

controlling channels $[\beta_{end}, \beta_{max}]$ of the fanbeam to be opened in sequence in a direction from $\beta_{end}$ to $\beta_{max}$ at the first velocity $V_1=\alpha-\beta_{max}$.

8. The method according to claim 7, wherein, in a case of $\alpha_{end}=\beta_{max}-\beta_{end}$, $\alpha_{max}=\pi+2\beta_{max}$ and a tomography scan, the method further comprises:

setting a weight $\omega(\alpha,\beta)$ of sampling data corresponding to the sampling angle $\alpha$ and the channel $\beta$ as follows:

$$\omega(\alpha,\beta) = \begin{cases} \dfrac{\alpha-h_1}{\alpha_2-h_1} & h_1 < \alpha < \alpha_2 \\ 1 & \alpha_2 \le \alpha < \alpha_3 \\ \dfrac{\alpha-h_2}{\alpha_3-h_2} & \alpha_3 \le \alpha < h_2 \\ 0 & \text{else} \end{cases},$$

wherein $h_1 = \max(0, \alpha_1)$, $\alpha_1 = \beta - \beta_{max} + \alpha_{end}$, $h_2 = \min(\alpha_4, \pi+2\beta_{max})$, $\alpha_4 = \beta + \beta_{max} + \pi + 2\beta_{max} - \alpha_{end}$, $\alpha_2 = \dfrac{4\beta_{max}-\alpha_{end}}{2\beta_{max}}(\beta+\beta_{max})$, and $\alpha_3 = \dfrac{4\beta_{max}-\alpha_{end}}{2\beta_{max}}(\beta+\beta_{max}) + \pi - 2\beta_{max} + \alpha_{end}$.

9. The method according to claim 1, wherein, in a case that channels $[-\beta_{max}, \beta_{end}]$ are open $(\beta_{end}, \beta_{max}]$ are close, and $\alpha_{end}=\beta_{max}-\beta_{end}$, controlling each of the channels of the fanbeam to be closed in sequence in a direction from $-\beta_{max}$ to $\beta_{max}$ at the second velocity comprises:

controlling preset channels $[-\beta_{max}, \beta_{end}]$ of the fanbeam to be closed in sequence in a direction from $-\beta_{max}$ to $\beta_{end}$ at the second velocity $V_2=\alpha-\beta_{max}-\pi$.

10. The method according to claim 9, wherein, in a case of $\alpha_{end}=\beta_{max}-\beta_{end}$, $\alpha_{max}=\pi+2\beta_{max}$ and a tomography scan, the method further comprises:

setting a weight $\omega(\alpha,\beta)$ of sampling data corresponding to the sampling angle $\alpha$ and the channel $\beta$ as follows:

$$\omega(\alpha,\beta) = \begin{cases} \dfrac{\alpha-h}{\alpha_2-h_1} & h_1 < \alpha < \alpha_2 \\ 1 & \alpha_2 \le \alpha < \alpha_3 \\ \dfrac{\alpha-h_2}{\alpha_3-h_2} & \alpha_3 \le \alpha < h_2 \\ 0 & \text{else} \end{cases},$$

wherein $h_1 = \max(0, \alpha_1)$, $\alpha_1 = \beta - \beta_{max} + \alpha_{end}$, $h_2 = \min(\alpha_4, \pi+2\beta_{max})$, $\alpha_4 = \beta + \beta_{max} + \pi + 2\beta_{max} - \alpha_{end}$, $\alpha_2 = \dfrac{4\beta_{max}-\alpha_{end}}{2\beta_{max}}(\beta+\beta_{max})$, and $\alpha_3 = \dfrac{4\beta_{max}-\alpha_{end}}{2\beta_{max}}(\beta+\beta_{max}) + \pi - 2\beta_{max} + \alpha_{end}$.

11. The method according to claim 1, wherein, in a case of $\alpha_{end}=\beta_{max}-\beta_{end}$, $\alpha_{max}=\pi+2\beta_{max}$ and a tomography scan, the method further comprises:

setting a weight $\omega(\alpha,\beta)$ of sampling data corresponding to the sampling angle $\alpha$ and the channel $\beta$ as follows:

$$\omega(\alpha,\beta) = \begin{cases} \dfrac{\alpha-h}{\alpha_2-h_1} & h_1 < \alpha < \alpha_2 \\ 1 & \alpha_2 \le \alpha < \alpha_3 \\ \dfrac{\alpha-h_2}{\alpha_3-h_2} & \alpha_3 \le \alpha < h_2 \\ 0 & \text{else} \end{cases},$$

wherein

-continued $$h_1 = \max(0, \alpha_1), \alpha_1 = \beta - \beta_{max} + \alpha_{end},$$

$$h_2 = \min(\alpha_4, \pi + 2\beta_{max}), \alpha_4 = \beta + \beta_{max} + \pi + 2\beta_{max} - \alpha_{end},$$

$$\alpha_2 = \frac{4\beta_{max} - \alpha_{end}}{2\beta_{max}}(\beta + \beta_{max}), \text{ and}$$

$$\alpha_3 = \frac{4\beta_{max} - \alpha_{end}}{2\beta_{max}}(\beta + \beta_{max}) + \pi - 2\beta_{max} + \alpha_{end}.$$

12. An apparatus for scanning with a lowered dose, comprising:
 a determining unit, configured to determine a dynamic changing model of a prepatient collimator according to a rotation angle of a tube in a scanning mode; and
 a control unit, configured to, in a case that the scanning mode is a normal scan, control an opening angle of the prepatient collimator according to the dynamic changing model of the prepatient collimator at an initial stage and an end stage of the normal scan; and
 the control unit is further configured to, in a case that the scanning mode is a scan with phase control, control an opening angle of the prepatient collimator according to the dynamic changing model of the prepatient collimator at an initial stage and an end stage of a phase of the scan with phase control,
 wherein the dynamic changing model of the prepatient collimator determined by the determining unit is a dynamic changing model of the prepatient collimator in a direction of an X-axis;
 in a fanbeam scanning, a sampling angle $\alpha$ is an angle between a positive direction of a Y-axis and a central channel of a fanbeam, wherein $\alpha$ is in a range of $[0, \alpha_{max}]$, $\alpha_{max} \geq \pi + 2\beta_{max}$; the fanbeam comprises channels in a range of $[-\beta_{max}, \beta_{max}]$ with the central channel as an axis; the control unit comprises:
 a first control sub-unit, configured to control each of the channels of the fanbeam to be opened in sequence in a direction from $-\beta_{max}$ to $\beta_{max}$ at a first velocity in a case that a is in a range of $[0, \alpha_{end}]$, wherein all of the channels of the fanbeam are open in a case of $\alpha = \alpha_{end}$; and/or
 a second control sub-unit, configured to control each of the channels of the fanbeam to be closed in sequence in a direction from $-\beta_{max}$ to $\beta_{max}$ at a second velocity in a case that a is in a range of $[\alpha_{max}-\alpha_{end}, \alpha_{max}]$, wherein all of the channels of the fanbeam are close in a case of $\alpha = \alpha_{max}$.

13. The apparatus according to claim 12, wherein
 the first control sub-unit is configured to control each of the channels of the fanbeam to be opened in sequence in a direction from $-\beta_{max}$ to $\beta_{max}$ at the first velocity $$V_1 = \frac{2\beta_{max}}{\alpha_{end}} * \alpha - \beta_{max}$$

in a case of $0 < \alpha_{end} \leq 2\beta_{max}$.

14. The apparatus according to claim 12, wherein
 the second control sub-unit is configured to control each of the channels of the fanbeam to be closed in sequence in a direction from $-\beta_{max}$ to $\beta_{max}$ at the second velocity $$V_2 = \frac{2\beta_{max}}{\alpha_{end}} * (\alpha - \alpha_{max}) + \beta_{max}$$

in a case of $0 < \alpha_{end} \leq 2\beta_{max}$.

15. The apparatus according to claim 12, wherein, in a case that channels $[-\beta_{max}, \beta_{end}]$ are open, channels $(\beta_{ends}, \beta_{max}]$ are close, and $\alpha_{end} = \beta_{max} - \beta_{end}$,
 the first control sub-unit is configured to control channels $[\beta_{end}, \beta_{max}]$ of the fanbeam to be opened in sequence in a direction from $\beta_{end}$ to $\beta_{max}$ at the first velocity $V_1 = \alpha - \beta_{max}$.

16. The apparatus according to claim 12, wherein, in a case that channels $[-\beta_{max}, \beta_{end}]$ are open, channels $(\beta_{end}, \beta_{max}]$ are close, and $\alpha_{end} = \beta_{max} - \beta_{end}$,
 the second control sub-unit is configured to control preset channels $[-\beta_{max}, \beta_{end}]$ max fiend of the fanbeam to be closed in sequence in a direction from $-\beta_{max}$ to $\beta_{end}$ at the second velocity $V_2 = \alpha - \beta_{max} - \pi$.

* * * * *